(12) United States Patent
Seto et al.

(10) Patent No.: US 9,167,954 B2
(45) Date of Patent: Oct. 27, 2015

(54) FLUID EJECTION DEVICE

(75) Inventors: Takeshi Seto, Chofu (JP); Kazuyoshi Takayama, Sendai (JP); Atsuhiro Nakagawa, Sendai (JP); Toru Nakano, Sendai (JP); Hiroaki Yamamoto, Sendai (JP)

(73) Assignee: Seiko Epson Corporation, Tokyo (JP)

( * ) Notice: Subject to any disclaimer, the term of this patent is extended or adjusted under 35 U.S.C. 154(b) by 191 days.

(21) Appl. No.: 13/416,214

(22) Filed: Mar. 9, 2012

(65) Prior Publication Data

US 2012/0232341 A1 Sep. 13, 2012

(30) Foreign Application Priority Data

Mar. 11, 2011 (JP) ................................ 2011-054002

(51) Int. Cl.
*A61B 17/20* (2006.01)
*A61N 1/30* (2006.01)
*A61B 18/18* (2006.01)
*A61B 17/32* (2006.01)
*A61B 1/00* (2006.01)
*A61B 1/015* (2006.01)
*A61B 1/12* (2006.01)
*A61B 17/3203* (2006.01)

(52) U.S. Cl.
CPC .......... *A61B 1/00091* (2013.01); *A61B 1/00087* (2013.01); *A61B 1/015* (2013.01); *A61B 1/126* (2013.01); *A61B 17/3203* (2013.01)

(58) Field of Classification Search
CPC ........ A61B 1/012; A61B 1/015; A61B 1/018; A61B 1/12; A61B 18/22; A61B 18/24; A61B 18/245; A61B 2217/005; A61B 2217/007; A61F 9/00745

USPC .......... 600/104, 106, 107, 127, 129, 156–159; 604/19; 606/2–19, 167–171; 607/88–95
See application file for complete search history.

(56) References Cited

U.S. PATENT DOCUMENTS

| | | | | |
|---|---|---|---|---|
| 5,135,482 | A | * | 8/1992 | Neracher .......................... 604/22 |
| 7,815,632 | B2 | * | 10/2010 | Hayakawa et al. ............. 606/14 |
| 2005/0124985 | A1 | | 6/2005 | Takayama et al. |
| 2008/0086077 | A1 | | 4/2008 | Seto et al. |
| 2009/0043320 | A1 | | 2/2009 | Seto et al. |

FOREIGN PATENT DOCUMENTS

| | | |
|---|---|---|
| JP | 2003-500098 | 1/2003 |
| JP | 2003-111766 | 4/2003 |
| JP | 2005-152094 | 6/2005 |
| JP | 2005-152127 | 6/2005 |
| JP | 2005-169094 | 6/2005 |

(Continued)

*Primary Examiner* — Ryan Henderson
(74) *Attorney, Agent, or Firm* — Workman Nydegger (57) ABSTRACT

A fluid ejection device includes a fluid chamber configured to store fluid, a nozzle configured to eject the fluid stored in the fluid chamber, a fluid supply channel connected to the fluid chamber and configured to supply the fluid to the fluid chamber, an air bubbles generating member configured to generate air bubbles in the fluid chamber, and a partitioning wall portion configured to separate the fluid chamber and the fluid supply channel, support the air bubbles generating member. The partitioning wall portion include at least one hole, communicating the fluid chamber and the fluid supply channel. The hole is configured to inhibit backflow during ejection of a jet pulse.

10 Claims, 8 Drawing Sheets

(56) References Cited

FOREIGN PATENT DOCUMENTS

| JP | 2008-082202 | 4/2008 |
| JP | 2009-108866 | 5/2009 |
| JP | 2009-299690 | 12/2009 |
| WO | WO 00/71038 | 11/2000 |

* cited by examiner

FLUID EJECTION DEVICE

This application claims priority to Japanese Application No. 2011-054002 filed Mar. 11, 2011, which application is incorporated by reference in its entirety.

BACKGROUND

1. Technical Field

Embodiments of the present invention relate to a fluid ejection device.

2. Related Art

A liquid jet knife configured to excise (dissect or debulk) a soft biological tissue by continuously ejecting a liquid (water, for example) from a nozzle at a high speed is an example of a medically used fluid ejection device. An excision method using this liquid jet knife is characterized by being free from heat damage and having high tissue selectivity, and is capable of preserving microscopic blood vessels or nerves. Therefore, therapies using this system, especially in abdominal surgeries, are in widespread clinical use.

However, because the above-described liquid jet knife uses a continuous flow of liquid, the amount of liquid ejected is significant. As a result, droplets of the liquid may splash outside of an operation site may occur and the amount of liquid ejected can make surgery difficult. In fact, the ability to maintain or secure visibility is difficult due to the generation of air bubbles or the accumulation of liquid (e.g., water) in the operation site.

Accordingly, a liquid pulse jet knife configured to eject liquid intermittently instead continuously has been proposed (for example, see JP-T-2003-500098 and JP-A-2003-111766). Since the liquid pulse jet knives described in these documents eject liquid intermittently, an impact pressure is generated instantaneously at a location where the ejected liquid hits. Therefore, a liquid pulse jet knife that ejects liquid intermittently can be used to perform excisions with a small amount of flow that are equivalent to the excisions performed with liquid jet knifes employing a continuous flow. Devices disclosed in JP-T-2003-500098 and JP-A-2003-111766 are configured to eject liquid by generating a vapor bubble. In JP-T-2003-500098, the vapor bubble is generated by electric discharge from an electrode, and in JP-A-2003-111766, the vapor bubble is generated by a laser.

In conventional pulse jet knives that use vapor bubbles to eject liquid, the fluid is pushed by the vapor bubbles towards the nozzle. However, the vapor bubbles also cause the fluid to flow contrary to the fluid supply direction. Therefore, a problem arises in that the speed and the amount of the fluid ejected from the nozzle is reduced (that is, the ejection intensity is lowered).

SUMMARY

An advantage of some aspects of the invention is to improve the ejection intensity of fluid in a fluid ejection device.

An embodiment of the invention is directed to a fluid ejection device that includes a fluid chamber configured to store fluid, a nozzle configured to eject the fluid stored in the fluid chamber, a fluid supply channel connected to the fluid chamber in a predetermined direction and configured to supply the fluid to the fluid chamber, an air bubbles generating member configured to generate air bubbles in the fluid chamber, and a partitioning wall portion configured to separate the fluid chamber and the fluid supply channel, support the air bubbles generating member, and include at least one hole communicating the fluid chamber and the fluid supply channel. In the fluid ejection device, a value obtained by dividing a total cross-sectional area of the hole in a cross section orthogonal to the predetermined direction by a length of the hole in the predetermined direction is smaller than a value obtained by dividing a cross-sectional area of the nozzle in the cross section by a length of the nozzle in the predetermined direction.

Other features of embodiments of the invention will be apparent by descriptions in the specification and the attached drawings.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

From the description in this specification and the attached drawings, at least the following matters become apparent.

One embodiment of the invention is directed to a fluid ejection device. The fluid ejection device may include a fluid chamber configured to store fluid, a nozzle configured to eject the fluid stored in the fluid chamber, a fluid supply channel connected to the fluid chamber in a predetermined direction and configured to supply the fluid to the fluid chamber, an air bubbles generating member configured to generate air bubbles in the fluid chamber, and a partitioning wall portion configured to separate the fluid chamber and the fluid supply channel, support the air bubbles generating member, and include at least one hole communicating the fluid chamber and the fluid supply channel. In one example a value obtained by dividing a total cross-sectional area of the hole in a cross section orthogonal to the predetermined direction by a length of the hole in the predetermined direction is smaller than a value obtained by dividing a cross-sectional area of the nozzle in the cross section by a length of the nozzle in the predetermined direction.

Because, in at least some embodiments, the value obtained by dividing the total cross-sectional area of the hole in a cross section orthogonal to the predetermined direction (the direction substantially parallel to the direction in which the fluid flows) by the length of the hole in the predetermined direction is smaller than the value obtained by dividing the cross-sectional area of the nozzle in the cross section by the length of the nozzle in the predetermined direction, the fluid tends to flow toward the nozzle rather than toward the hole when the air bubbles are generated. In other words, since the fluid does not easily flow into the hole (the reverse flow or flow in a direction contrary to the fluid flow is impeded and can hardly occur), the energy which generates the air bubbles can be used efficiently for the ejection of the fluid from the nozzle. In one example, the hole is configured such that it is difficult for the fluid to flow in a reverse direction. Therefore, the ejection intensity of the fluid is improved.

In one embodiment, the air bubbles generating member includes an optical fiber configured to generate air bubbles by emitting a laser into fluid. The optical fiber is supported by the partitioning wall portion so that a laser emitting surface projects into the fluid chamber.

According to the fluid ejection device as described above, since the laser emitting surface and the partitioning wall portion can be separated, damage to the partitioning wall portion can be easily prevented when the air bubbles are generated.

In one embodiment, the fluid ejection device includes a protecting portion configured to protect an area from the laser. The area may be from a predetermined position closer to the nozzle with respect to a connecting surface between the fluid chamber and the fluid supply channel to at least the partitioning wall portion from the laser.

In this configuration, since the area irradiated with the laser can be protected by the protecting portion, a material used for forming the fluid chamber may be a material which can easily be damaged by the laser.

In one example, the value obtained by dividing the cross-sectional area of the nozzle in the cross section by the length of the nozzle in the predetermined direction is larger than a constant multiple of the value obtained by dividing the total cross-sectional area of the hole in the cross section by the length of the hole in the predetermined direction of the hole. The constant may be a value equal to or smaller than 100.

According to the fluid ejection device as described above, an excessive increase in resistance in the fluid supply channel can be prevented, so that a stable supply of the fluid into the fluid chamber is achieved.

In the following embodiments, a liquid jet knife (hereinafter, also referred to as a water jet knife) which ejects liquid (water, for example) as a type of fluid will be exemplified in the description of a fluid ejection device.

First Embodiment
Configuration of Water Jet Knife

Figure 1:
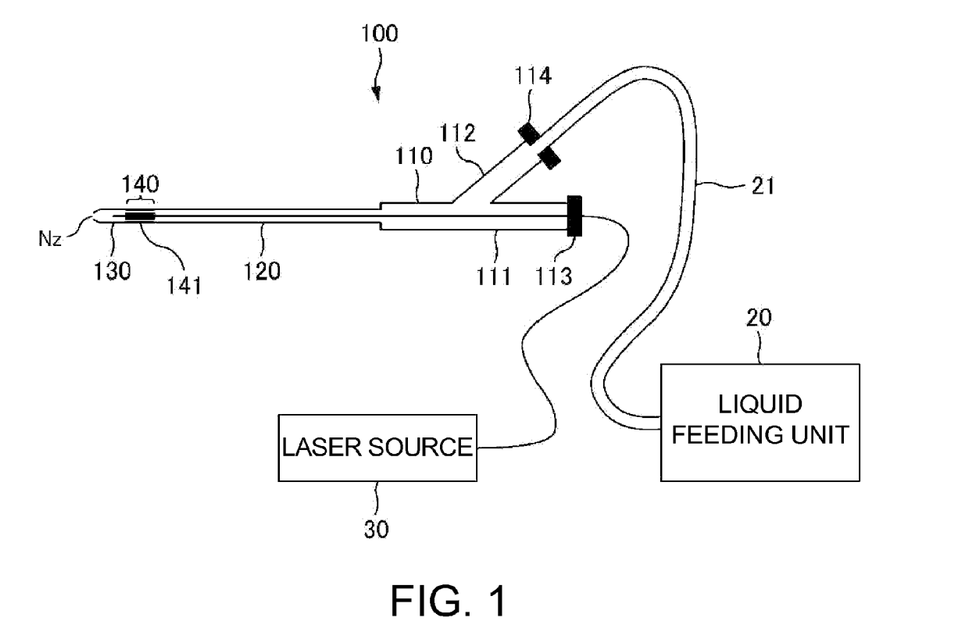
FIG. 1 is a schematic drawing showing a configuration of a water jet knife according to a first embodiment.
Figure 2:
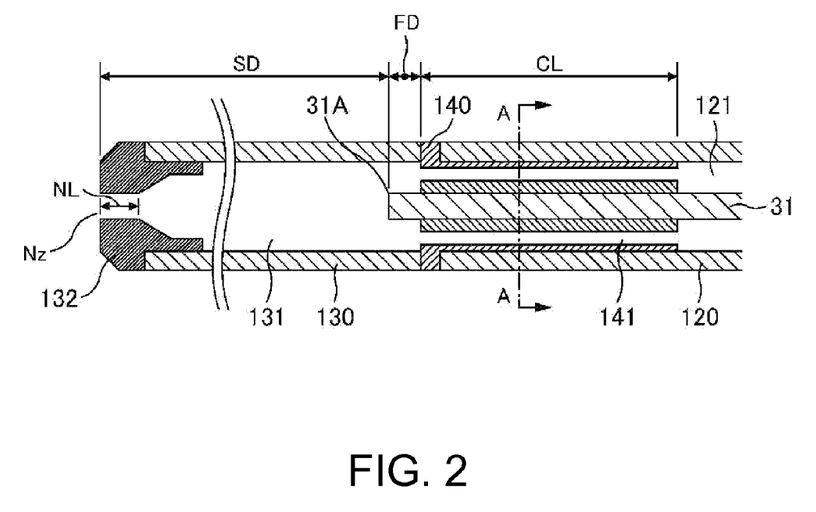
FIG. 2 is a drawing showing a structure of a cross-section of a distal end portion of the water jet knife taken in the longitudinal direction according to the first embodiment.
Figure 3:
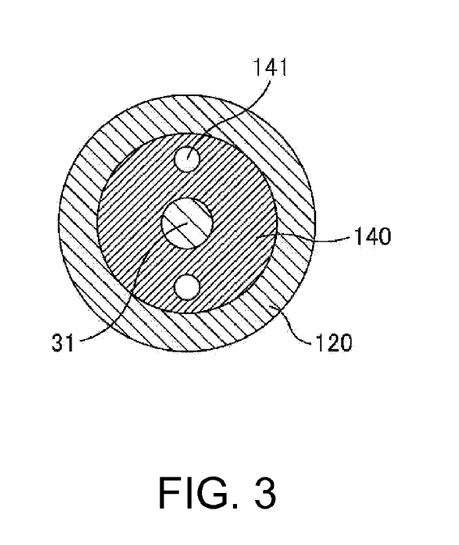
FIG. 3 is a cross-sectional view taken along the line A-A in FIG. 2.

FIG. 1 is a schematic drawing showing a configuration of a water jet knife 100 in a first embodiment. The water jet knife 100 in the first embodiment is configured to be held directly for excising an affected area. FIG. 2 is a drawing showing a structure of a cross-section of a distal end portion of the water jet knife 100 taken in the longitudinal direction according to the first embodiment, and FIG. 3 is a cross-sectional view taken along the line A-A in FIG. 2.

The water jet knife 100 in this embodiment shown in FIG. 1 includes a Y connector 110, a liquid supply pipe 120, a distal end pipe 130, and a partitioning wall member 140.

The Y connector 110 is a cylindrical member having a hollow cavity in the interior thereof, and includes a first tube portion 111, a second tube portion 112, an optical fiber fixing member 113, and a tube fixing member 114.

The first tube portion 111 constitutes a base portion of the Y connector 110.

The second tube portion 112 is provided so as to be branched from a midpoint of the first tube portion 111.

A soft connecting tube 21 extending from a liquid feeding unit 20 is connected to an opening of the second tube portion 112. The connecting tube 21 is fixed to the opening of the second tube portion 112 by the tube fixing member 114. Accordingly, a flow channel in the connecting tube 21 communicates with the hollow cavity in the interior of the Y connector 110. Liquid (water in this embodiment) is supplied from the liquid feeding unit 20 to the Y connector 110 through the connecting tube 21.

A silica based optical fiber 31, for example, is passed so as to penetrate through an opening at an end side (right side in the drawing) of the first tube portion 111 of the Y connector 110 through the optical fiber fixing member 113. Portions between the optical fiber 31 and the optical fiber fixing member 113 and between the optical fiber fixing member 113 and the Y connector 110 are sealed respectively so as not to allow leakage of the liquid. In other words, the optical fiber fixing member 113 is sealed with respect to the Y connector 110 and the optical fiber 31 to prevent the liquid introduced through the flow channel in the connecting tube 21 from leaking. The optical fiber 31 extends to the outside of the Y connector 110 and is connected to a laser source 30. In this embodiment, the laser source 30, which supplies pulsed light of Ho:YAG laser (wavelength 2.1 µm), is employed by way of example and not limitation.

The liquid supply pipe 120 is connected to the other end side (left side in the drawing) of the first tube portion 111 of the Y connector 110. As shown in FIG. 2, the partitioning wall member 140 having a flange portion is inserted and fixed to an end portion of the liquid supply pipe 120. Furthermore, the partitioning wall member 140 is connected to the distal end pipe 130. The liquid supply pipe 120, the partitioning wall member 140, and the distal end pipe 130 are fixed together. In one example outer peripheral portions of the liquid supply pipe 120, the partitioning wall member 140, and the distal end pipe 130 are welded together. In one example, the distal end pipe 130 is welded or otherwise connected to the partitioning wall member 140 and the partitioning wall member 140 is welded or otherwise connected to the end of the liquid supply pipe 120.

The liquid supply pipe 120 is configured to supply the liquid from the Y connector 110 to the distal end pipe 130. The liquid supply pipe 120 includes a supply flow channel 121 (which corresponds to a fluid supply channel). The supply flow channel 121 serves as a flow channel of the liquid in the interior thereof.

The partitioning wall member 140 (which corresponds to a partitioning wall portion) is provided so as to separate the liquid supply pipe 120 and the distal end pipe 130, and the optical fiber 31 is passed so as to penetrate through the center of the partitioning wall member 140. The partitioning wall member 140 supports the optical fiber 31 in this state (a state in which a distal end 31A of the optical fiber 31 projects into the interior of a liquid chamber 131). The distal end 31A of the optical fiber 31 is an example of a pulsed laser emitting surface. Capillary flow channels 141 (which correspond to holes) are provided on the outside of the optical fiber 31 in the partitioning wall member 140. The capillary flow channels 141 or holes connect or communicate the supply flow channel 121 of the liquid supply pipe 120 with the liquid chamber 131 (described later) of the distal end pipe 130. In this embodiment, two of the capillary flow channels 141 are provided on the outside (the upper side and the lower side of the optical fiber 31 in the drawing) of the optical fiber 31 as shown in the drawing. FIG. 3, for example, illustrates the capillary flow channels 141 provided on the upper and lower sides of the optical fiber 31.

The distal end pipe 130 includes the liquid chamber 131 (which corresponds to a fluid chamber in one example) configured to store the liquid. The liquid chamber 131 stores the liquid supplied from the Y connector 110 through the supply flow channel 121 of the liquid supply pipe 120 and the capillary flow channels 141 of the partitioning wall member 140. In addition, a nozzle member 132 having a nozzle Nz configured to eject the liquid stored in the liquid chamber 131 is fixed to an end portion (a distal end portion) of the distal end pipe 130. FIG. 2, for instance, illustrates the nozzle Nz fixed to the distal end portion of the distal end pipe 130.

Operation of Water Jet Knife

Figure 4A:
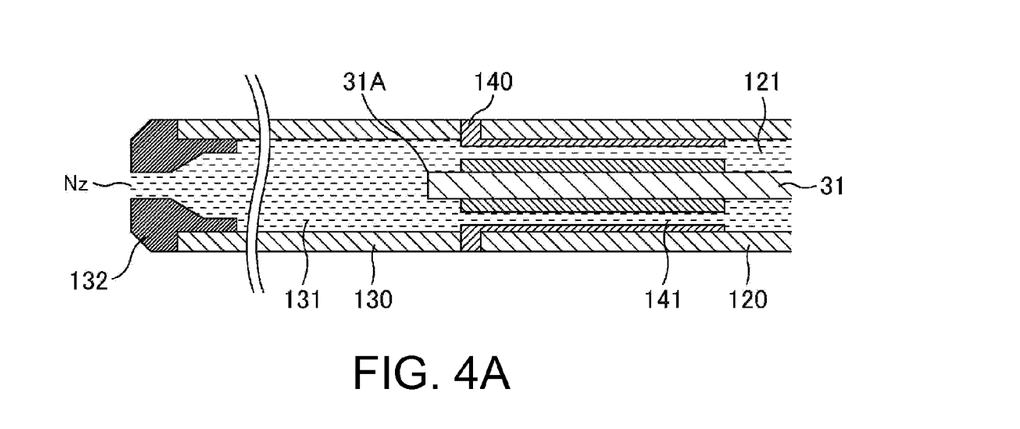
FIG. 4A and FIG. 4B are depict an operation of the water jet knife.
Figure 4B:
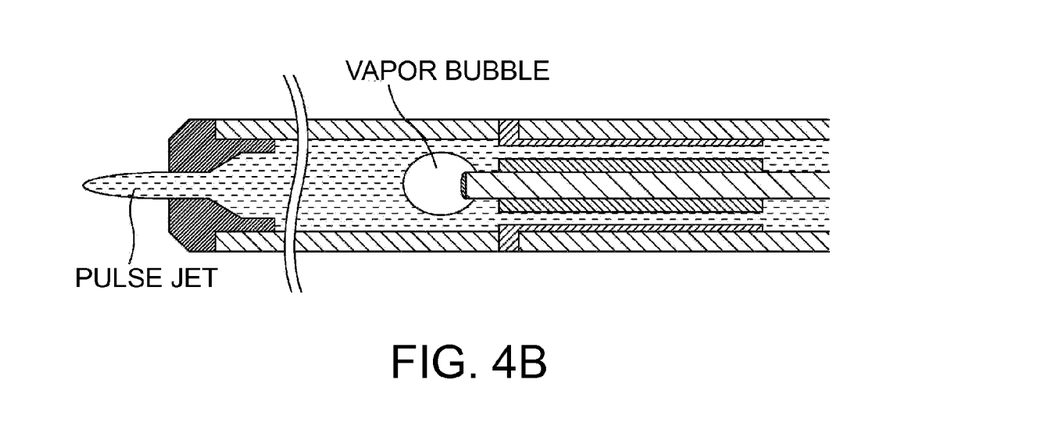

FIG. 4A and FIG. 4B illustrate an exemplary operation of the water jet knife 100. Referring now to FIG. 4A and FIG. 4B, an operation of the water jet knife 100 in this embodiment will be described.

During operation of the water jet knife 100 the liquid feeding unit 20 starts feeding the liquid to the water jet knife 100. Accordingly, the liquid is pumped into the Y connector 110 via the connecting tube 21. By feeding the liquid from the liquid feeding unit 20, a hollow cavity portion of the Y connector 110, the supply flow channel 121 of the liquid supply pipe 120, the capillary flow channels 141 of the partitioning wall member 140, and the liquid chamber 131 of the distal end pipe 130 are filled with the liquid in sequence as shown in FIG. 4A. Subsequently, the liquid starts to flow out from the nozzle Nz of the nozzle member 132. At this time, the flow rate of the liquid flowing from the nozzle Nz is small (by way of example only, 0.2 cc/s), and the speed is low (by way of example only, 1 m/s or slower). Since excision of tissues with such a flow is difficult, safety is ensured even when the liquid flows out from the nozzle Nz.

Subsequently, when the liquid chamber 131 is filled with the liquid and the liquid is irradiated with the pulsed laser from the distal end 31A of the optical fiber 31, the energy is absorbed by the liquid. As a result of absorbing the energy, the liquid is instantaneously evaporated as shown in FIG. 4B. Accordingly, a vapor bubble is generated around the distal end 31A of the optical fiber 31. The generation of the vapor bubble causes the internal pressure of the liquid chamber 131 to rise abruptly, and the liquid pressed by this pressure is ejected as a pulse jet at a burst from the nozzle Nz. The speed of ejection of the pulse jet ejected from the nozzle Nz at this time is as high as 10 m/s to 80 m/s, and is capable of excising tissue.

After the pulsed jet has been generated, a hollow cavity is partly formed in the liquid chamber 131. However, the liquid chamber 131 is filled with the liquid in a short time by the feed of liquid from the liquid feeding unit 20. The state shown in FIG. 4A is restored again, and the ejection of the pulse jet is enabled. As a result, pulse jets can be repeatedly ejected in accordance with the discussion herein.

In this embodiment, in order to generate the pulse jet efficiently with the energy of the laser, the capillary flow channels 141 are provided in the partitioning wall member 140. The capillary flow channel 141 has an effect of inhibiting the liquid from flowing from the liquid chamber 131 back to the supply flow channel 121 when the vapor bubble is formed. As a result, the ejection intensity of the pulse jet ejected from the nozzle Nz is enhanced. In other words, the flow of the liquid at least during operation of the knife is from the supply flow channel 121 to the liquid chamber 131. A reverse flow of the liquid from the liquid chamber 131 back to the supply flow channel 121 is inhibited by the capillary flow channel 141. Inhibiting back flow through the capillary flow channel 141 ensures that most of the energy generated with respect to the vapor bubbles is used to eject the jet. By inhibiting back flow, the energy needed to operate the device efficiently can be reduced since energy conventionally lost to the back flow is not used in ejection of the jet.

Relationship Between Nozzle and Capillary Flow Channel

A relationship between the nozzle Nz and the capillary flow channel(s) 141 will be described. In the following description, the flow of the liquid from the supply flow channel 121 to the nozzle Nz is defined as a normal direction, and the downstream side of the normal direction is referred to as the front and the upstream side is referred to as the rear.

The nozzle Nz includes a hole provided forward of the distal end 31A of the optical fiber 31, and the capillary flow channel 141 is a hole provided on the partitioning wall member 140 provided rearward of the distal end 31A of the optical fiber 31. When the vapor bubble is generated in the liquid chamber 131, the internal pressure in the liquid chamber 131 is increased. As a result of the increase in the internal pressure in the liquid chamber 131, a flow of the liquid toward the nozzle Nz and a flow of the liquid toward the capillary flow channels 141 are generated. The capillary flow channel 141 is configured such that the efficiency of ejection is increased at the nozzle and the flow back through the capillary flow channel 141 is inhibited.

Accordingly, an action when the liquid flows into the hole will be considered.

Figure 5:
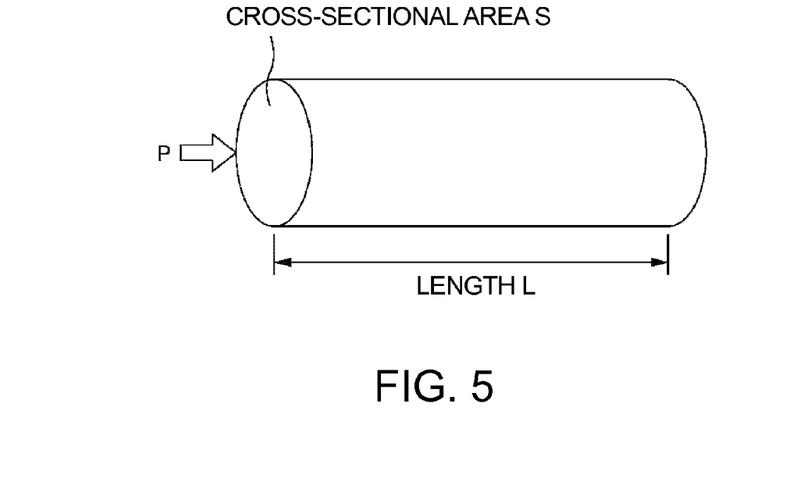
FIG. 5 depicts an action when the liquid flows into a hole.

FIG. 5 is a drawing for explaining the action when the liquid flows into the hole. Assuming that the flow channel has a constant cross section, a cross-sectional area is defined as S, the length as L, and the liquid density as $\rho$. It is assumed that a pressure difference $\Delta P$ (a pressure P) is generated at both ends of the flow channel. The liquid in the flow channel flows out by the application of the pressure P. The amount of change in flow rate per unit time is expressed by $\Delta Q$.

When the change in the speed of the liquid in the flow channel is defined as $\Delta u$, the value $\Delta Q$ is expressed by an expression $\Delta Q = S \cdot \Delta u$.

Therefore, as the equation of motion, the following relation is satisfied.

$$P \cdot S = S \cdot L \cdot \rho \cdot \Delta u \quad (1)$$

Therefore, the following relation is satisfied and the smaller the value S, or the larger the value L, the smaller the value $\Delta Q$ becomes (that is, the liquid can hardly flow or it is difficult for the liquid to flow).

$$\Delta Q = (P \cdot S)/(L \cdot \rho) \quad (2)$$

In order to prevent the reverse flow toward the supply flow channel 121 when the vapor bubble is generated in the liquid chamber 131, the value $\Delta Q$ on the upstream side (the capillary flow channels 141) of the liquid chamber 131 needs to be smaller than the value $\Delta Q$ on the downstream side (Nozzle Nz) thereof. Here, since the values $\rho$ and P are both the same, from the expression (2), it is necessary to satisfy the following relationship.

$$NS/NL > A \times CS/CL \quad (3)$$

In the relationship set forth in the expression (3), NS is a cross-sectional area of the nozzle, NL is the length, CL is a capillary length, and CS is a total cross-sectional area of the capillary (the sum of a plurality of capillaries).

The values NS and CS are the cross-sectional areas in the cross-section orthogonal to the direction substantially parallel to the direction of liquid flow, and the values NL and CL are the lengths in the direction substantially parallel to the direction of liquid flow. Here, A is a coefficient (constant), and in this embodiment, the coefficient A is set to be 1 or larger (e.g., 5 or larger). In this case, the amount of change of the flow rate (reverse flow) to the capillary flow channels 141 is smaller than the amount of change of the flow rate to the nozzle Nz. For example, when the coefficient A is 5, the amount of change of the flow rate to the capillary flow channels 141 is one-fifth the amount of change of the flow rate toward the nozzle Nz. Therefore, a larger part of the energy produced by the generation of the vapor bubble can be used for generating a jet of liquid or a pulse jet. Accordingly, the ejection intensity of the liquid from the nozzle Nz can be increased while preventing the reverse flow back through the capillary flow channel 141.

However, from the object of the excision, the diameter of the nozzle Nz is as small as the order of 0.1 mm to 0.8 mm (that is, the cross-sectional area NS is small). In order to ensure that the jet pulse travels straight ahead or substantially straight ahead, the length NL of the nozzle Nz needs to have at least a length on the order of one to five times the diameter (in some instances when the length NL is shorter than the range described above, the liquid ejected from the nozzle Nz does not travel straight ahead, but is spread out like a spray). In other words, in the expression (3), the value NS/NL is a very small value. Therefore, if the value of the coefficient A is too large, the value CS/CL is required to be an even smaller value. In this case, the flow of the liquid from the supply flow channel 121 to the liquid chamber 131 is impeded. IN other words, an increase in resistance in flow channel in the capillary flow channels 141 results, so that the liquid can hardly flow from the supply flow channel 121 side into the liquid chamber 131. Consequently, the load of the liquid feeding unit 20 is increased. From these reasons, the coefficient A is usually 100 or smaller.

Distance SD Between Nozzle and Distal End of Optical Fiber

A distance SD between the nozzle Nz and the distal end 31A of the optical fiber 31 is shown in FIG. 2. If the vapor bubble generated in the interior of the liquid chamber 131 goes out from the nozzle Nz, stabilization of the generation of the jet (or pulse jet) is impaired. Depending on the case, a pulsed laser beam having a high energy may go out from the nozzle Nz, which is quite dangerous. Therefore, a sufficient length should be provided to ensure that the laser beam is absorbed by the liquid in the liquid chamber 131. The distance SD from the distal end 31A of the optical fiber 31 to the nozzle Nz provides this assurance and ensures that the laser beam is absorbed by the liquid in the liquid chamber 131. More specifically, the distance SD is, by way of example and not limitation, 5 mm or larger. However, if the distance SD is too long, attenuation of energy occurs in the interior of the distal end pipe 130 (the interior of the liquid chamber 131). Therefore, the distance SD is, by way of example only and not limitation, 200 mm or smaller.

Distance FD Between Partitioning Wall and Distal End of Optical Fiber

A distance FD between the partitioning wall member 140 and the distal end 31A of the optical fiber 31 is also shown in FIG. 2. The vapor bubble generated in the distal end 31A of the optical fiber 31 spreads not only forward of the distal end 31A but also rearward of the distal end 31A. Therefore, if the distance FD is small, the partitioning wall member 140 may become damaged when the pulsed laser is emitted from the distal end 31A. Accordingly, in order to avoid causing the partitioning wall member 140 from being damaged at the time of emission of the pulsed laser, the distal end 31A of the optical fiber 31 is configured to project with respect to the partitioning wall member 140, by way of example and not limitation, by 0.5 mm or more. In other words, the distance FD between the partitioning wall member 140 and the distal end 31A of the optical fiber 31 may be 0.5 mm or larger. However, the distal end 31A of the optical fiber 31 may vibrate at the time the vapor bubble is generated if the distance FD is too long. As a result, the distance FD is, by way of example and not limitation, mm or smaller. This range for FD ensures that the partitioning wall member 140 is not damaged during generation of the vapor bubbles and also ensures that vibration is substantially eliminated or not present during generation of the vapor bubbles.

As described above, the water jet knife 100 includes the liquid chamber 131 configured to store the liquid (water), the nozzle Nz configured to eject the liquid stored in the liquid chamber 131, the supply flow channel 121 configured to supply the liquid to the liquid chamber 131, the optical fiber 31 configured to generate air or vapor bubbles in the liquid, and the partitioning wall member 140 configured to separate the liquid chamber 131 and the supply flow channel 121. The partitioning wall member 140 supports the optical fiber 31 so that the vapor bubble is generated in the liquid chamber 131, and the capillary flow channels 141 communicating the liquid chamber 131 and the supply flow channel 121. There may be more than one or more capillary flow channels (e.g., two capillary flow channels).

In a configuration that includes two capillary flow channels, the value obtained by dividing the total cross-sectional area CS of the two capillary flow channels 141 by the length CL of the capillary flow channels 141 is set to be smaller than the value obtained by dividing the cross-sectional area NS of the nozzle Nz by the length NL of the nozzle Nz. In this configuration, a reverse flow of liquid can hardly occur and most of the energy produced by the generation of the vapor bubble can be used for generation of the jet. Accordingly, improvement of the ejection intensity of the liquid from the nozzle Nz is achieved. By inhibiting a reverse flow of the liquid through the capillary flow channels, the energy of the laser for obtaining an equivalent ejection intensity (e.g., compared to conventional devices) can be reduced.

Second Embodiment

Figure 6:
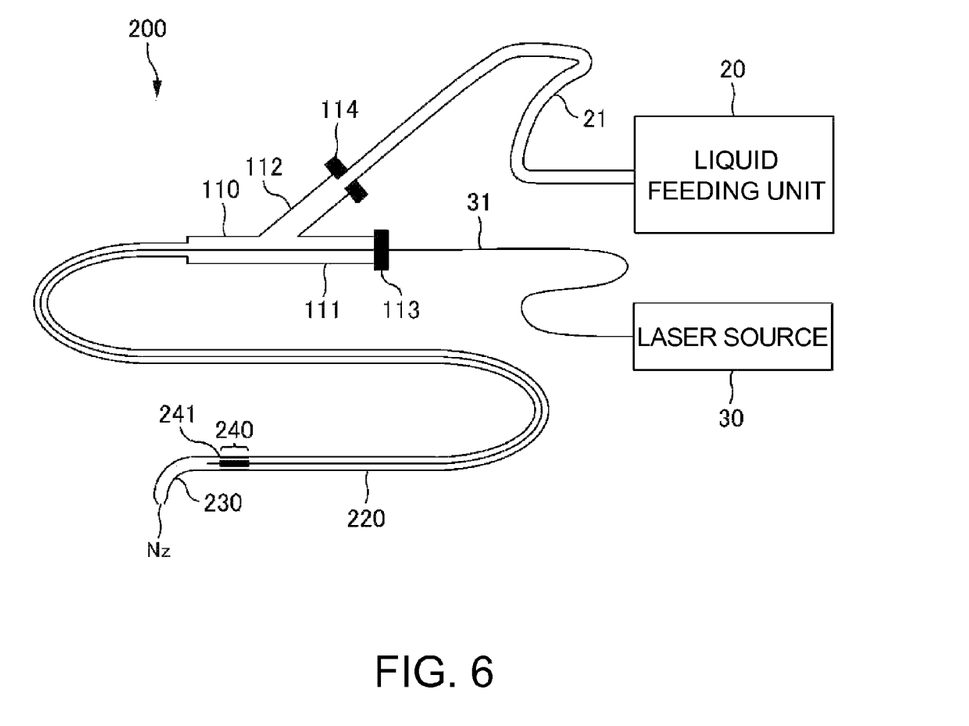
FIG. 6 is a schematic drawing showing a configuration of a water jet knife according to a second embodiment.

FIG. 6 is a schematic drawing showing a configuration of a water jet knife 200 according to a second embodiment. In FIG. 6, portions having the same configuration as those in the first embodiment (FIG. 1) are designated by the same reference numerals, and the corresponding description will be omitted.

The water jet knife 200 according to the second embodiment is a fluid ejection device provided in an endoscope unit including an endoscope and can be for a therapy or a surgical operation for biological bodies. The water jet knife 200 is configured to be inserted into a biological body (human, animal, etc.) for an endoscopic operation. In order to allow insertion into the body of the biological body, the water jet knife 200 according to the second embodiment may include or use a soft liquid supply tube 220 and a distal end tube 230 instead of the liquid supply pipe 120 and the distal end pipe 130 in the first embodiment.

Figure 7:
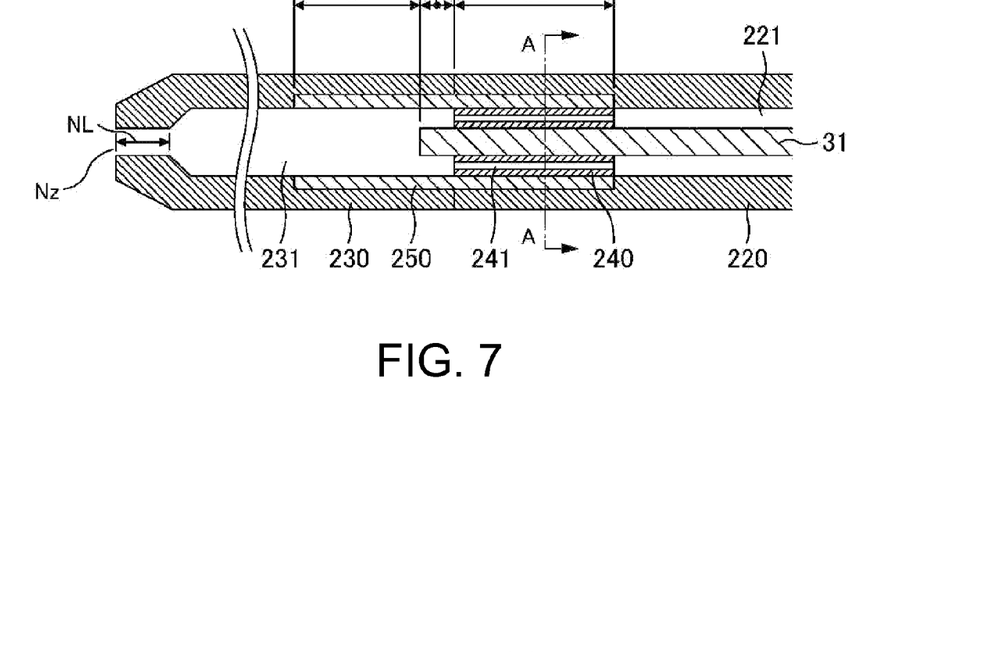
FIG. 7 is a drawing showing a structure of a cross-section of a distal end portion of the water jet knife taken in the longitudinal direction according to the second embodiment.
Figure 8:
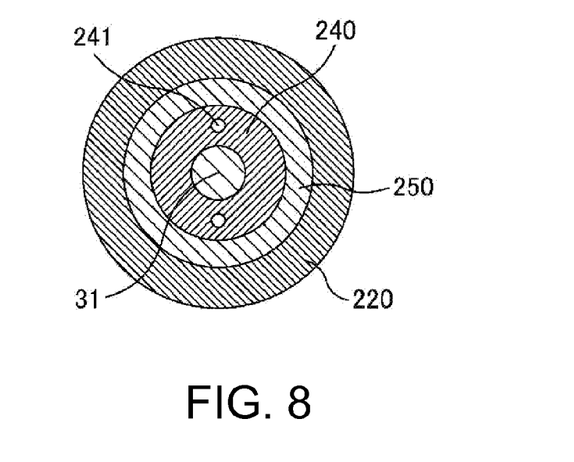
FIG. 8 is a cross-sectional view taken along the line A-A in FIG. 7.

FIG. 7 is a drawing showing a structure of a cross-section of a distal end portion of the water jet knife 200 taken in the longitudinal direction according to the second embodiment, and FIG. 8 is a cross-sectional view taken along the line A-A in FIG. 7. The water jet knife 200 includes the liquid supply tube 220, the distal end tube 230, a partitioning wall member 240, and a protection pipe 250.

The liquid supply tube 220 is configured to supply liquid from the Y connector 110 side toward the distal end tube 230, and includes a supply flow channel 221 which serves as a flow channel of the liquid in the interior of the liquid supply tube 220.

The partitioning wall member 240 is provided so as to separate the liquid supply tube 220 and the distal end tube 230, and the optical fiber 31 is passed so as to penetrate through the center of the partitioning wall member 240. The partitioning wall member 240 supports the optical fiber 31 in this state (in a state in which the distal end 31A of the optical fiber 31 projects toward the distal end tube 230). Capillary flow channels 241 are provided on the outside of the optical fiber 31 in the partitioning wall member 240. The capillary flow channels 241 connect or communicate the supply flow channel 221 of the liquid supply tube 220 with a liquid chamber 231 of the distal end tube 230. In this embodiment, in the partitioning wall member 240, two of the capillary flow channels 241 are provided on the outside of the optical fiber 31 as shown in the FIG. 8.

The distal end tube 230 includes the liquid chamber 231. The liquid chamber 231 is configured to store the liquid. In the liquid chamber 231, liquid is supplied from the Y connector 110 through the supply flow channel 221 of the liquid supply tube 220 and the capillary flow channels 241 of the partitioning wall member 240. In addition, the nozzle Nz, which is configured to eject the liquid stored in the liquid chamber 231, is provided at an end portion (a distal end portion) of the distal end tube 230.

The protection pipe 250 is inserted into both the liquid supply tube 220 and the distal end tube 230 and connects the liquid supply tube 220 and the distal end tube 230 by heat welding. The portions of the both tubes where the protection pipe 250 is formed are preferably formed to be thinner than other portions of the tubes so as to match the outer diameter of the protection pipe 250. This prevents the area of the knife 220 at a location of the protection pipe 250 from becoming an obstacle when inserting the water jet knife 200 into a forceps port 43 of the endoscope, described later.

The protection pipe 250 is configured to protect the distal end tube 230 and the liquid supply tube 220, which may be formed of a resin, from the pulsed laser. In the second embodiment, since the protection pipe 250 is provided, resins may be used as a material which forms the liquid chamber 231 (that is, the distal end tube 230).

The partitioning wall member 240 is press-fit and fixed in the protection pipe 250. The partitioning wall member 240 in the second embodiment also supports the optical fiber 31 at the center in the same manner as the partitioning wall member 140 in the first embodiment. Provided on the outside of the optical fiber 31 in the partitioning wall member 240 is the capillary flow channel 241 communicating the supply flow channel 221 of the liquid supply tube 220 and the liquid chamber 231 of the distal end tube 230. The partitioning wall member, like the partitioning wall member 140, includes holes or capillary flow channels formed therein as well as a space to accommodate the optical fiber 31. The optical fiber 31 is typically sealed such that leakage of the fluid does not occur around the optical fiber 31. In this embodiment, the protection pipe 250 and the partitioning wall member 240 are formed of a material having a high thermal resistance property such as metal and ceramic.

The operation of the water jet knife 200 (the operation of liquid ejection) in the second embodiment is the same as that in the first embodiment. Therefore, description will not be given here.

Figure 9:
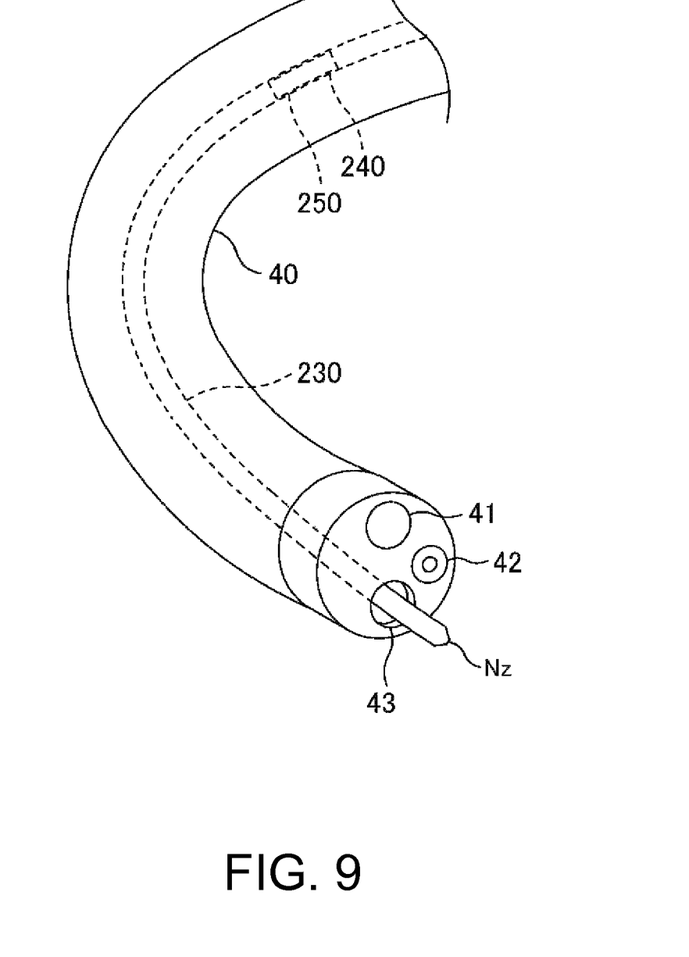
FIG. 9 is a schematic drawing showing a case where the water jet knife is applied to an endoscope.

FIG. 9 is a schematic drawing showing an example in which the water jet knife 200 in the second embodiment is applied to the endoscope.

The endoscope includes an operating unit (not shown), an insertion portion (not shown), and a distal end portion 40. The operating unit is a portion to be held by an operator of the endoscope during an operation. The insertion portion is a portion extending from the operating unit and configured to be inserted into the body. The insertion portion has plasticity and can be passively bent. The distal end portion 40 is provided at a distal end of the insertion portion and is configured to be remotely operated from the operating unit to control the bending movement.

As shown in FIG. 9, the distal end portion 40 of the endoscope includes an image pickup device 41, an irradiating portion 42, and a forceps port 43.

The image pickup device 41 is configured to pickup an image of a state of internal organs by, for example, a color video.

The irradiating portion 42 is configured to illuminate the interior of the body by light from a light source (not shown) so as to allow an inspection or a therapy to be performed smoothly.

The forceps port 43 is an opening for allowing passage of a medical tool used for sampling or treatment of tissue or collecting an abnormal substance or the like. In this embodiment, the water jet knife 200 is passed through the forceps port 43.

As described above, the distal end portion 40 is bent by the operation from the operating unit. In order to not hinder the bending movement (so as to allow the bending movement in the distal end portion 40), the liquid supply tube 220 and the distal end tube 230 used for the water jet knife 200 are formed of soft resin.

In the endoscope, since the curvature of the distal end portion 40 is increased, the protection pipe 250 is preferably positioned at the insertion portion of the endoscope (that is, on the back side of the distal end portion 40). In addition, since the insertion portion is also bent, it is useful to set a length PL of the protection pipe 250 shown in FIG. 7 to be as short as possible. The length PL may be, by way of example only and not limitation, 20 mm or smaller or 10 mm or smaller.

At the same time, the protection pipe 250 is intended to protect the distal end tube 230 and the liquid supply tube 220, which may be formed of a resin, from the pulsed laser. Therefore, at least 2 mm (or 5 mm) is required as a protecting distance GD. More specifically, the protection pipe 250 extends past an end face of the optical fiber 31 by at least 2 mm or by at least 5 mm or other distance.

The relationship between the nozzle Nz and the capillary flow channels 241 (that is, the relationship between NS/NL and CS/CL), and the range of the length of the distance FD is the same as in the first embodiment.

As described thus far, the water jet knife 200 in the second embodiment can be applied to or used in the endoscope. According to the water jet knife 200 in the second embodiment, most of or a larger part of the energy produced by the generation of the vapor bubble can be used for the generation of the jet as in the first embodiment. In other words, a reverse flow of the liquid from the liquid chamber 321 to the supply flow channel 221 can be prevented. Advantageously, improvement of the ejection intensity of the liquid from the nozzle Nz is achieved. Accordingly, an endoscopic operation such as the excision of an affected area while preserving blood vessels can be achieved.

Modification of the Second Embodiment

Figure 10A:
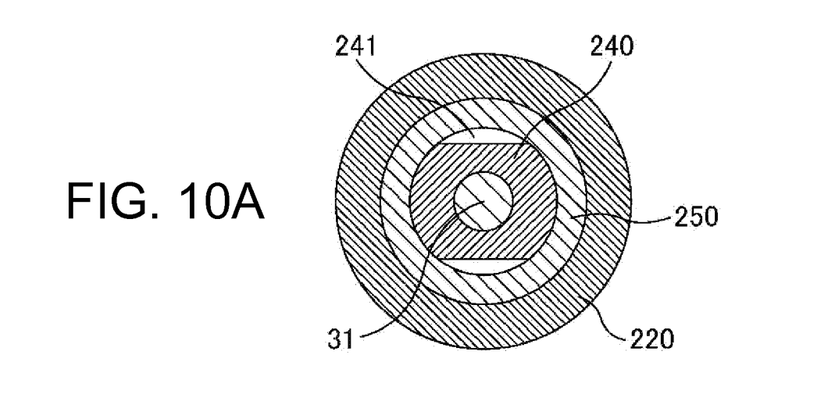
FIG. 10A illustrates a modification showing a partitioning wall member of the water jet knife.
Figure 10B:
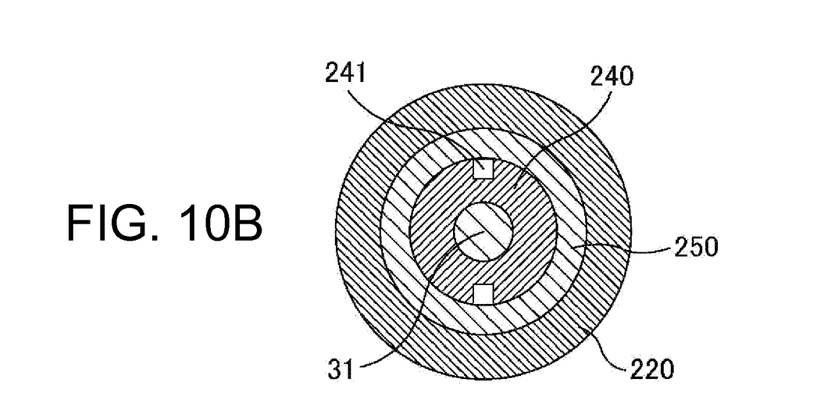
FIG. 10B illustrates another modification showing the partitioning wall member of the water jet knife.

FIG. 10A and FIG. 10B illustrate a modification of the partitioning wall member 240 of the water jet knife 200.

In FIG. 10A, the partitioning wall member 240 is formed into a shape in which parts (an upper end and a lower end) of an outer periphery are cut off straightly. The capillary flow channels 241 are thus formed between the partitioning wall member 240 and the protection pipe 250. More specifically, the capillary flow channels 241 are bounded by both the protection pipe 250 and the partitioning wall member 240. Therefore, the capillary flow channel 241 of the modification shown in FIG. 10A has a cross section in an arcuate shape instead of a circular shape.

In the example of FIG. 10B, the partitioning wall member 240 is formed into a shape in which parts (upper and lower ends) of the outer periphery are cut off into a rectangular shape. Therefore, the capillary flow channels 241 of the modification shown in FIG. 10B are formed into substantially a square shape between the partitioning wall member 240 and the protection pipe 250. The capillary flow channels illustrated in FIGS. 10A and 10B can be included in any of the embodiments discussed herein. Additional configurations of the capillary flow channels are also contemplated.

In such a modification as illustrated in FIGS. 10A and 10B, in the same manner as the embodiments described above, the relationship between the total cross-sectional area (CS) and the length (CL) of the capillary flow channels 241 is to be set so as to satisfy the above-described expression (3). In this configuration, improvement of the ejecting strength of the liquid is achieved.

As in this modification, when the capillary flow channels 241 are formed between the outer periphery of the partitioning wall member 240 and the protection pipe 250, the manufacture is simplified in comparison with the case where the capillary flow channels are formed by punching the partitioning wall member 240 as in the embodiment described above.

Figure 11:
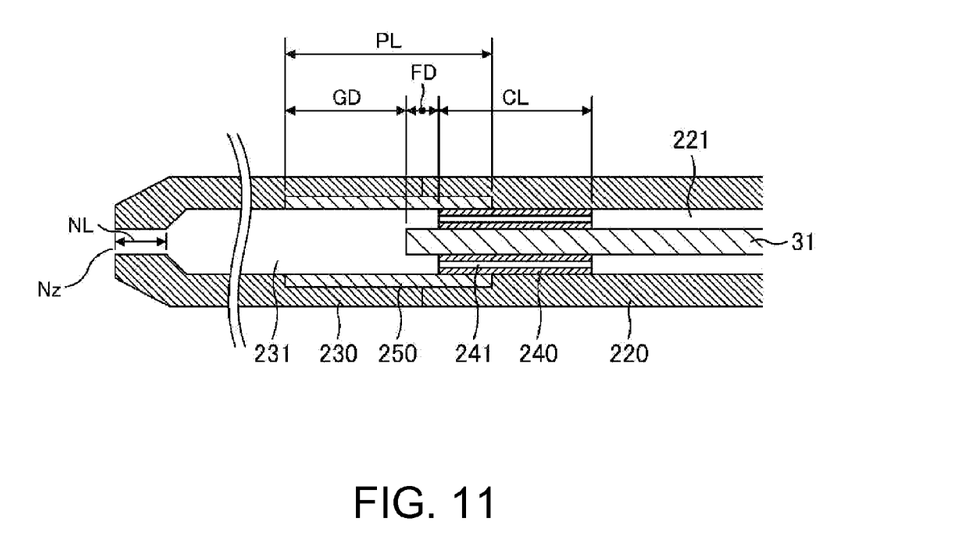
FIG. 11 shows a modification of a protection pipe of the water jet knife.

FIG. 11 illustrates a modification of the protection pipe 250 of the water jet knife 200 according to the second embodiment.

In this modification, a length (PL) of the protection pipe 250 is shorter than the length of the protection pipe shown in FIG. 7. The protection pipe 250 shown in FIG. 11 is provided in an area from a position closer to the nozzle Nz than an end surface (a connecting surface between the liquid chamber 231 and the supply flow channel 221) on the front side of the partitioning wall member 240 (the downstream side of the flow channel) to at least the partitioning wall member 240. Accordingly, the distal end tube 230 and the liquid supply tube 220 can be protected from the pulsed laser.

In the modification shown in FIG. 11, a boundary between the distal end tube 230 and the liquid supply tube 220 is different from the case shown in FIG. 7. More specifically, the boundary between the distal end tube 230 and the liquid supply tube 220 is different relative to the position of the end portion of the partitioning wall member 240. In this manner, the boundary between the distal end tube 230 and the liquid supply tube 220 may be different from the position of the end portion of the partitioning wall member 240.

The protection pipe 250 and the partitioning wall member 240 may be formed integrally. Furthermore, although the capillary flow channels 241 are provided on the partitioning wall member 240 in this embodiment, the invention is not limited thereto and the capillary flow channel may be provided, for example, on or in the protection pipe 250.

Other Embodiment

The embodiments described herein are intended to facilitate understanding of the invention, and are not intended to limit the comprehension of the invention. Embodiments of the invention may be modified or improved without departing the scope of the invention, and the invention includes equivalents as a matter of course.

Fluid Ejection Device

Although the water jet knife has been described as an example in the embodiments described above, the invention is not limited thereto, and may be applied to other types of fluid ejection devices.

Fluid

Although water has been used as the fluid in the embodiments described above, the invention is not limited thereto, and physiologic saline may be used. Other liquids such as blood or gas such as water vapor or nitrogen may be used. In this case, a laser having an absorption band according to the type of the fluid may be used.

Optical Fiber

In the embodiments described above, although the vapor bubble has been generated using the optical fiber 31, the invention is not limited thereto. For example, the vapor bubble may be generated using electric discharge from an electrode, or the vapor bubble may be generated by using a heater.

What is claimed is:
1. A fluid ejection medical device comprising:
a fluid chamber configured to store fluid;
a nozzle configured to eject the fluid stored in the fluid chamber;
a fluid supply channel connected to the fluid chamber and configured to supply the fluid to the fluid chamber;
an air bubbles generating member configured to generate air bubbles in the fluid chamber; and
a partitioning wall portion configured to separate the fluid chamber and the fluid supply channel, support the air bubbles generating member, and include at least one hole communicating the fluid chamber and the fluid supply channel,
wherein a portion of the air bubble generating member is configured to project into the fluid chamber a distance beyond the partitioning wall portion such that the projected portion is not surrounded by the partitioning wall portion, the projected portion being a distance from the nozzle such that the projecting portion does not project into the nozzle,
wherein a value obtained by dividing a total cross-sectional area of the at least one hole in a cross section of the at least one hole orthogonal to a longitudinal direction of the at least one hole by a length of the at least one hole in the longitudinal direction of the at least one hole is smaller than a value obtained by dividing a cross-sectional area of the nozzle in a plane parallel to the cross section by a length of the nozzle in the longitudinal direction of the at least one hole,
wherein the air bubbles generating member is an optical fiber configured to generate air bubbles by emitting a laser into fluid.
2. The fluid ejection medical device according to claim 1, wherein the optical fiber is supported by the partitioning wall portion so that a laser emitting surface projects into the fluid chamber by a range from not less than 0.5 mm to not more than 5 mm.

3. The fluid ejection medical device according to claim 2, further comprising:

a protecting portion configured to protect an area from a predetermined position closer to the nozzle with respect to a connecting surface between the fluid chamber and the fluid supply channel to at least the partitioning wall portion from the laser.

4. The fluid ejection medical device according to claim 1, wherein the value obtained by dividing the cross-sectional area of the nozzle in the cross section by the length of the nozzle in the longitudinal direction of the at least one hole is larger than a constant multiple of the value obtained by dividing the total cross-sectional area of the at least one hole in the cross section by the length of the at least one hole in the longitudinal direction of the at least one hole, and the constant is a value falling within a range from not less than 1 to not more than 100.

5. A surgical apparatus comprising the fluid ejection medical device according to claim 1.

6. A surgical apparatus comprising the fluid ejection medical device according to claim 2.

7. The surgical apparatus comprising the fluid ejection medical device according to claim 3.

8. The surgical apparatus according to claim 5, further comprising:

an image pickup device configured to be used for image pickup;

an irradiating portion including a light source; and a forceps port configured to be used for allowing a medical tool to be passed therethrough.

9. The surgical apparatus according to claim 6, further comprising:

an image pickup device configured to be used for image pickup;

an irradiating portion including a light source; and a forceps port configured to be used for allowing a medical tool to be passed therethrough.

10. The surgical apparatus according to claim 7, further comprising:

an image pickup device configured to be used for image pickup;

an irradiating portion including a light source; and a forceps port configured to be used for allowing a medical tool to be passed therethrough.

* * * * *